United States Patent [19]

Friedman et al.

[11] Patent Number: 5,659,095

[45] Date of Patent: Aug. 19, 1997

[54] COMPOSITION FOR INHIBITING THE POLYMERIZATION OF AROMATIC VINYL MONOMERS

[75] Inventors: Howard Stephen Friedman, North Haven; Gerald John Abruscato, Southington; John Matthew DeMassa, S. Norwalk; Anthony Vincent Gentile, Waterbury; Anthony Vincent Grossi, Torrington, all of Conn.

[73] Assignee: Uniroyal Chemical Company, Inc., Middlebury, Conn.

[21] Appl. No.: 615,663

[22] Filed: Mar. 13, 1996

[51] Int. Cl.$^6$ ........................................ C07C 7/20
[52] U.S. Cl. ........................ 585/5; 585/1; 585/2; 585/3; 585/4; 585/860; 208/48 AA; 203/6; 203/7; 203/8; 203/9; 203/58; 203/65; 203/68; 203/69; 203/70
[58] Field of Search ........................ 585/1, 2, 3, 4, 585/5, 860; 208/48 AA; 203/6, 7, 8, 9, 58, 65, 68, 69, 70

[56] References Cited

U.S. PATENT DOCUMENTS

| | | | |
|---|---|---|---|
| 2,526,567 | 10/1950 | Drake. | |
| 3,723,555 | 3/1973 | Armbrust et al. | 585/406 |
| 4,105,506 | 8/1978 | Watson | 203/9 |
| 4,376,678 | 3/1983 | Partos | 585/4 |
| 4,468,343 | 8/1984 | Butler | 252/403 |

FOREIGN PATENT DOCUMENTS

| | | |
|---|---|---|
| 52-102231 | 8/1977 | Japan. |
| 52-133931 | 11/1977 | Japan. |
| 0504765 | 4/1939 | United Kingdom. |

*Primary Examiner*—Glenn A. Caldarola
*Assistant Examiner*—Elizabeth D. Wood
*Attorney, Agent, or Firm*—Daniel Reitenbach

[57] ABSTRACT

A polymerization inhibitor composition for inhibiting the polymerization of aromatic vinyl monomers at elevated temperatures comprising:

(a) a benzofuroxan derivative of the formula

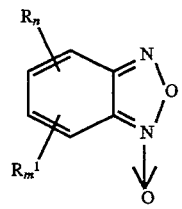

wherein R is $C_1$–$C_4$ alkyl or alkoxy; $R^1$ is a nitro group; and m and n are each independently 0, 1, or 2; and (b) a solvent selected from the group consisting of toluene, xylene, ethylbenzene, vinyltoluene, divinylbenzene, alpha-methylstyrene, and a $C_{12}$–$C_{18}$ hydrocarbon, and methods for inhibiting the polymerization of aromatic vinyl monomers at elevated temperatures using this composition.

13 Claims, No Drawings

COMPOSITION FOR INHIBITING THE POLYMERIZATION OF AROMATIC VINYL MONOMERS

FIELD OF THE INVENTION

This invention relates to a polymerization inhibitor composition for inhibiting the polymerization of aromatic vinyl monomers at elevated temperatures comprising a benzofuroxan derivative and certain aromatic or aliphatic hydrocarbon solvents. This invention also relates to a method for inhibiting the polymerization of an aromatic vinyl monomer at elevated temperatures, which comprises subjecting the aromatic vinyl monomer to the elevated temperatures in the presence of the polymerization inhibitor composition.

BACKGROUND OF THE INVENTION

Commercial processes for the manufacture of vinyl aromatic compounds such as monomeric styrene, divinyl benzene and lower alkylated styrenes (such as alpha-methylstyrene and vinyl toluene) typically produce products contaminated with various impurities, such as benzene, toluene, and the like. These impurities must be removed in order for the monomer product to be suitable for commercial applications. Such purification of vinyl aromatic compounds is generally accomplished by distillation.

It is, however, well known that vinyl aromatic monomers polymerize readily and that the rate of polymerization increases rapidly as the temperature increases. In order to prevent polymerization of the vinyl aromatic monomer under distillation conditions, various polymerization inhibitors have been employed.

Dinitrophenols have been described as useful to inhibit the polymerization of vinyl aromatic monomers. U.S. Pat. No. 2,526,567 describes the stabilization of chlorostyrenes using 2,6-dinitrophenols. U.S. Pat. No. 4,105,506 describes the use of 2,6-dinitro-p-cresol as a polymerization inhibitor for vinyl aromatic compounds.

Dinitrophenols, however, are solids that are unstable at temperatures above their melting points and can explode at such temperatures. U.S. Pat. No. 4,664,845 describes the use of phenylenediamine solubilizers for dinitrophenols in aromatic solvents, to enable shipment of the dinitrophenols in liquid form.

U.S. Pat. No. 4,633,026 describes the use of certain alkyl-substituted phenylenediamines and phenothiazine compounds in the presence of air, as polymerization inhibitors.

U.S. Pat. No. 4,477,374 describes the use of an oxygenated phenylenediamine for polymerization inhibition of vinyl aromatic compounds. U.S. Pat. No. 4,915,873 describes the use of a phenothiazine compound and an aryl-substituted phenylenediamine, to stabilize vinyl aromatic compounds against polymerization.

Japanese Kokai Patent No. 52-102231 describes the use of benzofuroxan derivatives alone to inhibit polymerization of aromatic vinyl monomers. Japanese Kokai Patent No. 52-133931 describes an improved process for inhibition of polymerization of vinyl aromatic compounds, characterized by a combination of benzofuroxan or a derivative thereof, with a co-inhibitor chosen from benzoquinone dioximes or dinitrophenols.

Prior to the present invention, the use of benzofuroxan derivatives to inhibit styrene polymerization was difficult because benzofuroxan derivatives are unstable in styrene.

Additionally, since benzofuroxan derivatives are solid in form, their use in vinyl aromatic monomer distillation operations was impractical.

Accordingly, it is an object of this invention to provide a polymerization inhibitor composition for inhibiting the polymerization of aromatic vinyl monomers at elevated temperatures which comprises benzofuroxan or a derivative thereof. It is a further object of this invention to provide a method for inhibiting the polymerization of aromatic vinyl monomers at elevated temperatures using the polymerization inhibitor composition.

SUMMARY OF THE INVENTION

This invention relates to a polymerization inhibitor composition for inhibiting the polymerization of an aromatic vinyl monomer, such as styrene, at elevated temperatures, such as during distillation of the aromatic vinyl monomer, comprising:

(a) an effective amount of a benzofuroxan derivative of the formula

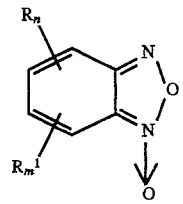

wherein R is $C_1$–$C_4$ alkyl or alkoxy; $R^m$ is a nitro group; and m and n are each independently 0, 1, or 2; and (b) a solvent selected from the group consisting of toluene, xylene, ethylbenzene, vinyltoluene, divinylbenzene, alpha-methylstyrene, and a $C_{12}$–$C_{18}$ hydrocarbon.

This invention also relates to a method for inhibiting the polymerization of an aromatic vinyl monomer, such as styrene, at elevated temperatures, such as during distillation of the aromatic vinyl monomer, which comprises subjecting the aromatic vinyl monomer to the elevated temperatures in the presence of an effective amount of a polymerization inhibitor composition comprising:

(a) an effective amount of a benzofuroxan derivative of the formula

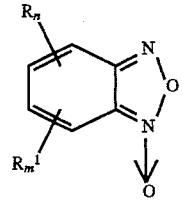

wherein R is $C_1$–$C_4$ alkyl or alkoxy; $R^m$ is a nitro group; and m and n are each independently 0, 1, or 2; and (b) a solvent selected from the group consisting of toluene, xylene, ethylbenzene, vinyltoluene, divinylbenzene, alpha-methylstyrene, and a $C_{12}$–$C_{18}$ hydrocarbon.

DETAILED DESCRIPTION OF THE INVENTION

The aromatic vinyl monomers can be styrene, substituted styrene, divinylbenzene, vinyltoluene, vinyl naphthalene, polyvinylbenzenes, and isomers thereof. Preferably, the aromatic vinyl monomer is styrene.

For the purposes of this invention, "elevated temperatures" means temperatures above room temperature.

Preferably, the elevated temperatures are those necessary for the distillation of the aromatic vinyl monomer.

Preferably, R is methyl or methoxy.

Preferred benzofuroxan derivatives include benzofuroxan-1-oxide, 4-nitrobenzofuroxan-1-oxide, 4,6-dinitrobenzofuroxan-1-oxide, 5-methylbenzofuroxan-1-oxide, 5-methyl-4-nitrobenzofuroxan-1-oxide, 5-methyl-4,6-dinitrobenzofuroxan-1-oxide, 5-methoxybenzofuroxan-1-oxide, 5-methoxy-4-nitrobenzofuroxan-1-oxide, 5-methoxy-4,6-dinitrobenzofuroxan-1-oxide, and the like.

Preferred solvents are xylene or ethylbenzene. Ethylbenzene is particularly preferred.

Generally, the weight of the benzofuroxan derivative in the solvent in the composition of this invention, can range from about 0.01% to about 20% by Weight. A preferred weight percent of the benzofuroxan derivative in the solvent is from about 15% to about 20%.

The effective amount of the benzofuroxan derivative can vary depending on the aromatic vinyl monomer, temperature, degree of inhibition of polymerization desired, etc., but is, in general, about 50 ppm to about 3000 ppm, preferably, about 100 ppm to about 1500 ppm by weight of the aromatic vinyl monomer. Accordingly, an effective amount of the composition of this invention is that amount which will supply about 50 ppm to about 3000 ppm, preferably, about 100 ppm to about 1500 ppm, by weight, of the benzofuroxan derivative to the aromatic vinyl monomer.

In actual commercial use, the polymerization inhibitor composition can be supplied to an aromatic vinyl monomer distillation system as needed. As stated above, the amount of polymerization inhibitor composition used can vary depending on the equipment, process, and capacity of the production set-up. The polymerization inhibitor composition can be readily fed into the aromatic vinyl monomer reactor distillation column.

The temperature of the distillation of the aromatic vinyl monomer can vary in a similar manner. For example, the temperatures for vinyl aromatic monomer distillation can range from about 75° C. to about 150° C., preferably from about 85° C. to about 125° C. The polymerization inhibitor composition of this invention is useful throughout this temperature range.

The polymerization inhibitor composition of this invention can be prepared by adding the desired amount of the benzofuroxan derivative, and any other stabilizing compound, in any order, to a measured amount of the solvent. If it is desirable to inhibit the polymerization of aromatic vinyl monomer both in the absence and presence of air, the polymerization inhibitor composition of the instant invention (which is anaerobic) can be combined with other polymerization inhibitors which are active in air. Preferably, such addition takes place under agitation.

The following examples are provided to illustrate this invention.

EXAMPLE 1

Qualitative Aging Study of Benzofuroxan-1-oxide in Various Solvents

In Table 1 below, compositions comprising benzofuroxan-1-oxide, which was purchased from the Aldrich Chemical Company, Milwaukee, Wis. (Benzofuroxan-1-oxide, 98%) and one of three solvents, ethyl benzene, xylenes, and styrene, were prepared wherein the benzofuroxan-1-oxide was present in the composition in an amount of 20 weight percent (w/w). Composition 1 contained benzofuroxan-1-oxide dissolved in ethylbenzene; Composition 2 contained benzofuroxan-1-oxide dissolved in xylene; and Comparative Composition A contained benzofuroxan-1-oxide dissolved in styrene.

The changes in color and the changes in other physical appearances of the compositions were noted and are summarized in Table 1 below.

TABLE 1

AGING STUDY

| Comp. No. | Solvent | Day 1 | Day 4 | Day 6 | Day 15 | Day 39 |
|---|---|---|---|---|---|---|
| 1 | Ethyl Benzene | No visible change | No visible change | No visible change | No visible change | Darker yellow; sediment |
| 2 | Xylene | Yellow; sediment | No visible change | No visible change | No visible change | Yellow; sediment |
| A | Styrene | Deep red; slight sediment | Deeper red color; Crystal ppt. | Solution is dark brown; Crystals | Solution is dark brown; yellowish crystal formation | Solution is dark brown; yellowish crystal formation |

The results from Comparative Composition A indicate that benzofuroxan derivatives are not stable in styrene. The sedimentation and crystal formation would be dangerous and unsuitable for a polymerization inhibitor in commercial use since the solids formed would clog pipes and other distillation equipment.

EXAMPLE 2

Static Screening of Benzofuroxan Compositions Containing Various Solvents

The compositions described in Example 1 above, were tested for polymerization inhibition of styrene.

Each of three flasks was charged with 40 grams of styrene to which was added a sufficient amount of one of the compositions of Example 1 to provide 100 ppm of benzofuroxan-1-oxide in the flask. The compositions were each aged as described above in Example 1 for 42 days and for 56 days. Each flask was then fitted with magnetic stirrers and septum closures and heated in an oil bath to 118° C. (plus or minus 2° C.). Each flask was purged with approximately 5 cc/min air run beneath the liquid surface during the period of the test. During the test period, samples were removed from each flask every one-half hour and tested for degree of polymerization by measuring the changes in refractive index.

Table 2 below, lists the induction time (time to reach 1% polymerization, weight of polymer/weight of styrene), in minutes, and the percent polymer measured, by weight.

TABLE 2

RESULTS OF STATIC POLYMERIZATION OF INHIBITION STUDIES

| Composition No. (42 day aging) | Induction Time* | % Polymerization |
|---|---|---|
| 1 | 58 | 1.16 |
| 2 | 67 | 2.16 |
| A | 30 | 1.16 |

TABLE 2-continued

RESULTS OF STATIC POLYMERIZATION OF INHIBITION STUDIES

| Composition No. (42 day aging) | Induction Time* | % Polymerization |
|---|---|---|
| Coposition No. (56 day aging) | | |
| 1 | 62 | 1.16 |
| 2 | 66 | 1.83 |
| A | 47 | 1.16 |

*Industry standard for acceptable vinyl aromatic inhibition is an induction time of about 60 minutes (induction time for styrene polymerization at 118° C. using dinitro-para-cresol at a concentration of 100 ppm as the polymerization inhibitor As can be seen from the results of Example 2, Comparative Composition A, containing benzofuroxan-1-oxide in styrene, did not perform as well as the Compositions 1 and 2, containing benzofuroxan-1-oxide and xylene, and benzofuroxan-1-oxide and ethylbenzene, respectively. The induction times for styrene using Comparative Composition A as a polymerization inhibitor, are much less than the 60 minute industry standard.

EXAMPLE 3

Characterization of the Degradation Product of Benzofuroxan-1-oxide in Styrene

The precipitate was collected from Comparative Composition A, washed with hexane, and then dried. The melting point of this solid was 143–144° C. NMR analysis of a wet sample of this solid indicated a structure similar to styrene.

Further spectroscopic (mass spec) and elemental analysis (52.66% C, 4.31% H, 19.05% N, and 17.63% O) indicate that the precipitate is 1,2-benzodioxime, the reaction product of benzofuroxan and styrene, having the following structure:

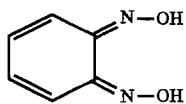

What is claimed is:

1. A polymerization inhibitor composition for inhibiting the polymerization of an aromatic vinyl monomer at elevated temperatures comprising:

(a) an effective amount of a benzofuroxan derivative of the formula

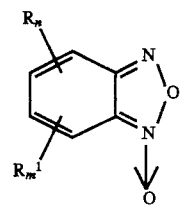

wherein R is $C_1$–$C_4$ alkyl or alkoxy; $R^1$ is a nitro group; and m and n are each independently 0, 1, or 2; and (b) a solvent selected from the group consisting of toluene, xylene, ethylbenzene, vinyltoluene, divinylbenzene, alpha-methylstyrene, and a $C_{12}$–$C_{18}$ hydrocarbon, wherein the concentration of the benzofuroxan derivative to the solvent is about 0.01% to about 20% by weight.

2. A polymerization inhibitor composition as recited in claim 1 wherein the concentration of the benzofuroxan derivative to the solvent is about 15% to about 20% by weight.

3. A polymerization inhibitor composition as recited in claim 1 wherein R is methyl or methoxy.

4. A polymerization inhibitor composition as recited in claim 1 wherein the benzofuroxan derivative is selected from the group consisting of benzofuroxan-1-oxide, 4-nitrobenzofuroxan-1-oxide, 4,6-dinitrobenzofuroxan-1-oxide, 5-methylbenzofuroxan-1-oxide, 5-methyl-4-nitrobenzofuroxan-1-oxide, 5-methyl-4,6-dinitrobenzofuroxan-1-oxide, 5-methoxybenzofuroxan-1-oxide, 5-methoxy-4-nitrobenzofuroxan-1-oxide, and 5-methoxy-4,6-dinitrobenzofuroxan-1-oxide.

5. A polymerization inhibitor composition as recited in claim 4 wherein the benzofuroxan derivative is benzofuroxan-1-oxide and the solvent is ethylbenzene.

6. A method for inhibiting the polymerization of an aromatic vinyl monomer at a temperature above room temperature, which comprises subjecting the aromatic vinyl monomer to the temperature above room temperature in the presence of an effective amount of a polymerization inhibitor composition comprising:

(a) an effective amount of a benzofuroxan derivative of the formula

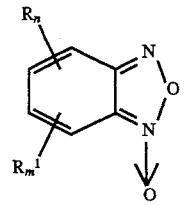

wherein R is $C_1$–$C_4$ alkyl or alkoxy; $R^1$ is a nitro group; and m and n are each independently 0, 1, or 2; and (b) a solvent selected from the group consisting of toluene, xylene, ethylbenzene, vinyltoluene, divinylbenzene, alpha-methylstyrene, and a $C_{12}$–$C_{18}$ hydrocarbon, wherein the concentration of the benzofuroxan derivative to the solvent is between about 0.01% and 20% by weight.

7. A method as recited in claim 6 wherein the temperature above room temperature is a temperature useful in the distillation of the aromatic vinyl monomer.

8. A method as recited in claim 6 wherein R is methyl or methoxy.

9. A method as recited in claim 6 wherein the benzofuroxan derivative is selected from the group consisting of benzofuroxan-1-oxide, 4-nitrobenzofuroxan-1-oxide, 4,6-dinitro-benzofuroxan-1-oxide, 5-methylbenzofuroxan-1-oxide, 5-methyl-4-nitrobenzofuroxan-1-oxide, 5-methyl-4,6-dinitrobenzofuroxan-1-oxide, 5-methoxybenzofuroxan-1-oxide, 5-methoxy-4-nitrobenzofuroxan-1-oxide, and 5-methoxy-4,6-dinitrobenzofuroxan-1-oxide.

10. A method as recited in claim 6 wherein the aromatic vinyl monomer is styrene.

11. A method as recited in claim 10 wherein the benzofuroxan derivative is benzofuroxan-1-oxide and the solvent is ethylbenzene.

12. In a method for inhibiting the polymerization of an aromatic-vinyl monomer during distillation of the aromatic vinyl monomer using a benzofuroxan derivative as a polymerization inhibitor, the improvement comprising distilling the aromatic vinyl monomer in the presence of an effective mount of a polymerization inhibitor composition comprising:

(a) an effective amount of a benzofuroxan derivative of the formula

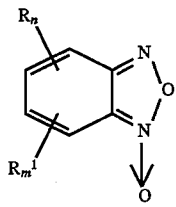

wherein R is $C_1$–$C_4$ alkyl or alkoxy; $R^1$ is a nitro group; and m and n are each independently 0, 1, or 2; and (b) a solvent selected from the group consisting of toluene; xylene, ethylbenzene, vinyltoluene, divinylbenzene, alpha-methylstyrene, and a $C_{12}$–$C_{18}$ hydrocarbon, wherein the concentration of the benzofuroxan derivative to the solvent is between about 0.01% and 20% by weight.

13. A method as recited in claim 12 wherein the aromatic vinyl monomer is styrene.

* * * * *